(12) United States Patent
Douglas

(10) Patent No.: US 7,211,068 B2
(45) Date of Patent: *May 1, 2007

(54) INFUSION DEVICE HAVING OFFSET FLOW PATH

(75) Inventor: Joel S. Douglas, Groton, CT (US)

(73) Assignee: Sterling Medivations, Inc., Norcross, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/190,740

(22) Filed: Jul. 27, 2005

(65) Prior Publication Data

US 2005/0267441 A1    Dec. 1, 2005

Related U.S. Application Data

(62) Division of application No. 10/814,950, filed on Mar. 30, 2004, now Pat. No. 6,923,791.

(60) Provisional application No. 60/459,252, filed on Mar. 31, 2003.

(51) Int. Cl.
*A61M 5/178* (2006.01)
*A61M 11/00* (2006.01)

(52) U.S. Cl. .................. 604/167.05; 604/93.01

(58) Field of Classification Search ............ 604/93.01, 604/164.11, 165.04, 167.01, 167.03, 167.04, 604/167.05, 167.06, 533, 534, 539

See application file for complete search history.

(56) References Cited

U.S. PATENT DOCUMENTS

| 4,755,173 | A | * | 7/1988 | Konopka et al. | ...... 604/167.02 |
| 5,176,662 | A | | 1/1993 | Bartholomew et al. | |
| 5,562,617 | A | * | 10/1996 | Finch et al. | ........... 604/288.02 |
| 5,968,011 | A | | 10/1999 | Larsen et al. | |
| 6,056,718 | A | | 5/2000 | Funderburk et al. | |
| 6,302,866 | B1 | * | 10/2001 | Marggi | ...................... 604/174 |
| 6,685,674 | B2 | | 2/2004 | Douglas et al. | |

* cited by examiner

*Primary Examiner*—Sharon E. Kennedy
(74) *Attorney, Agent, or Firm*—Altera Law Group, LLC

(57) ABSTRACT

An infusion device, including: a housing; an infusion cannula extending downwardly away from the housing and capable of receiving an insertion needle; a septum disposed in the housing; a passageway under said septum and in fluid communication with said cannula; and, an infusion needle insertable through the septum, the infusion needle capable of penetrating the septum and entering said passageway thereby forming a flow path between the infusion needle and the infusion cannula and wherein the ion cannula and the infusion needle are aligned on separate non identical axes.

18 Claims, 12 Drawing Sheets

INFUSION DEVICE HAVING OFFSET FLOW PATH

RELATED APPLICATION

This application is a divisional of application Ser. No. 10/814950, filed Mar. 30, 2004, issued on Aug. 2, 2005 as U.S. Pat. No. 6,923,791 which claims priority under 35 U.S.C. Section 119 to U.S. Provisional Application No. 60/459252, entitled Device For Subcutaneous Medication Using An Offset Flow Path, filed on Mar. 31, 2003, the complete disclosure of which is incorporated herein by reference in its entirety for all purposes.

TECHNICAL FIELD

The present invention is related to infusion devices, including insulin or other medication infusion devices that are positioned directly on a patient's skin.

BACKGROUND OF THE INVENTION

Numerous medication infusion devices which sit directly on top of a patient's skin have been developed. Such devices typically operate as follows. A housing of the device is placed on the patient's skin such that an infusion cannula (extending downwardly therefrom) pierces through the patient's skin. Typically, the housing is placed against the patient's skin by use of an inserter needle assembly. Specifically, an insertion needle on the inserter needle assembly is received through the housing, passing through the center of the infusion cannula. The main body of the inserter needle assembly is then used to press down against the housing, pushing the housing down against the patient's skin while the inserter needle guides the infusion cannula into the patient. Then, the inserter needle assembly is removed, pulling the inserter needle out of the housing, and leaving the hollow infusion cannula in the patient for delivery of medication therethrough. Then, a connecting hub is typically attached onto the housing. Fluid medication is then infused into the connecting hub, passing sequentially through the housing and the infusion cannula and into the patient. Examples of such systems are found in U.S. Pat. Nos. 6,056,718 and 6,685,674.

As can be seen, a problem common to these systems is that both the inserter needle and an infusion needle (in the connecting hub) pass through the septum in the same location. This is due to the fact that in existing designs, the infusion cannula, inserter needle, and infusion needle are all co-linear with one another.

A disadvantage of this common design is that the septum must be pierced in the same location by both the inserter needle (which is removed after the housing is placed onto the patient's skin) and the infusion needle (which passes through the septum when the connecting hub is attached to the housing). Re-using the same location in the septum for two different needle entries has the potential for causing septum wear and leakage. As will be further explained herein, other disadvantages of such "in-line" designs also exist.

SUMMARY OF THE INVENTION

The present invention provides an infusion device, having: a housing; an infusion cannula extending downwardly away from the housing and capable of receiving an insertion needle; a septum disposed in the housing; a passageway under said septum and in fluid communication with said cannula; and, an infusion needle insertable through the septum, the infusion needle capable of penetrating the septum and entering said passageway thereby forming a flow path between the infusion needle and the infusion cannula and wherein the infusion cannula and the infusion needle are aligned on separate non identical axes. Such axes may be parallel, in different planes relative to one another or at oblique angles relative to one another. The infusion needle is positioned to penetrate the septum thereby forming a flow path between the infusion needle and the infusion cannula when the connecting hub is attached to the housing.

In accordance with the present invention, the infusion cannula and the infusion needle are disposed off-axis to one another. For example, the infusion cannula and the infusion needle may be positioned parallel to one another. In preferred embodiments, the infusion needle is disposed in the center of the connecting hub and the infusion cannula is disposed off-center in the housing; however, the present invention is not so limited.

In accordance with the present invention, the infusion needle (in the connecting hub) passes through the septum at a location different from where an insertion needle (in the infusion cannula) passes through the septum. An advantage of this design is that there is significantly reduced potential for leakage since the insertion needle (used to initially position the infusion cannula in the patient) passes through the septum at a location different from the location where the infusion needle passes through the septum.

A further advantage of the present invention is that in embodiments where the infusion needle is positioned at the center of the connecting hub, the connecting hub can be rotatable with respect to the housing. This gives the patient greater comfort and flexibility since an infusion tube extending from the connecting hub can be rotated to different radial positions, as desired. As will be explained, the present connecting hub can be rotatable with respect to the housing through a full 360 degrees, some through amount less than 360 degrees, or alternatively, not be rotatable at all.

Another advantage of the present invention is that there is no torque on the infusion cannula when the connecting hub is rotated. This is particularly advantageous since the infusion cannula is received into the patient. Torque on the infusion cannula would cause irritation to the patient.

Another advantage of the present invention is that the infusion needle and infusion cannula may be of different diameters. Thus, different connecting hubs having different diameter infusion needles (e.g.: with different flow rates therethrough) can be interchangeably used with a single housing sitting on the patient's skin.

Another advantage of the present invention is that, by placing the infusion needle and the infusion cannula parallel to one another, the overall height of the assembled device can be reduced as compared to that of a standard "in-line" co-linear design.

DETAILED DESCRIPTION OF THE DRAWINGS

Figure 1:
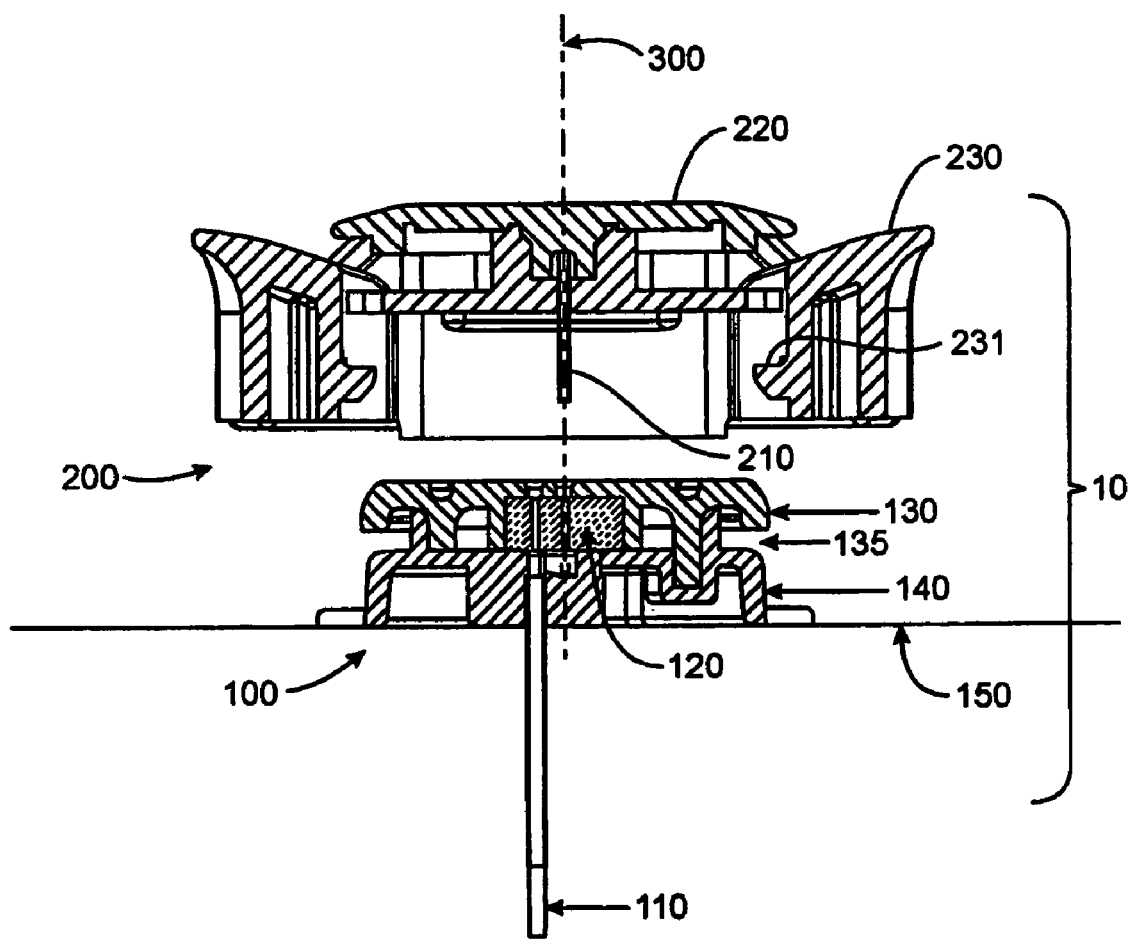
FIG. 1 is a sectional side elevation view of the present invention, prior to attaching the connecting hub onto the housing.

The present invention provides an infusion device having an "offset" design in which an infusion cannula (which is received into a patient's skin) is not co-linear with an infusion needle (which extends from a removable connecting hub), as follows:

Referring first to FIG. 1, an infusion device 10 is provided. Infusion device 10 includes a housing 100 which is positioned against a patient's skin. Specifically, an adhesive bandage 150 extends outwardly from housing 100 and an infusion cannula 110 extends downwardly away from housing 100. Infusion cannula 110 pierces through the patient's skin when adhesive bandage 150 is affixed to the patient's skin. A septum 120 is disposed within housing 100. In the illustrated embodiment, septum 120 is disposed between lower portion 140 and upper portion 130; however, the present invention is not so limited.

A connecting hub 200 is also provided. Connecting hub 200 includes a main body 220 and an infusion needle 210 extending downwardly therefrom, and a pair of flexible handles 230. As can be seen, infusion needle 210 is preferably co-linear with axis 300. (In the illustrated embodiment, axis 300 passes through the center of both connecting hub 200 and housing 100). As can therefore be seen, infusion cannula 110 is not co-linear with axis 300.

Connecting hub 200 is configured to be attached by a user directly on top of housing 100. This is seen clearly in FIG. 2. To securely connect connecting hub 200 onto housing 100, flexible handles 230 may be used. In the illustrated embodiment, each of flexible handles 230 includes a tab 231 which is received into a small notch 135 formed between lower portion 140 and upper portion 130.

Figure 2:
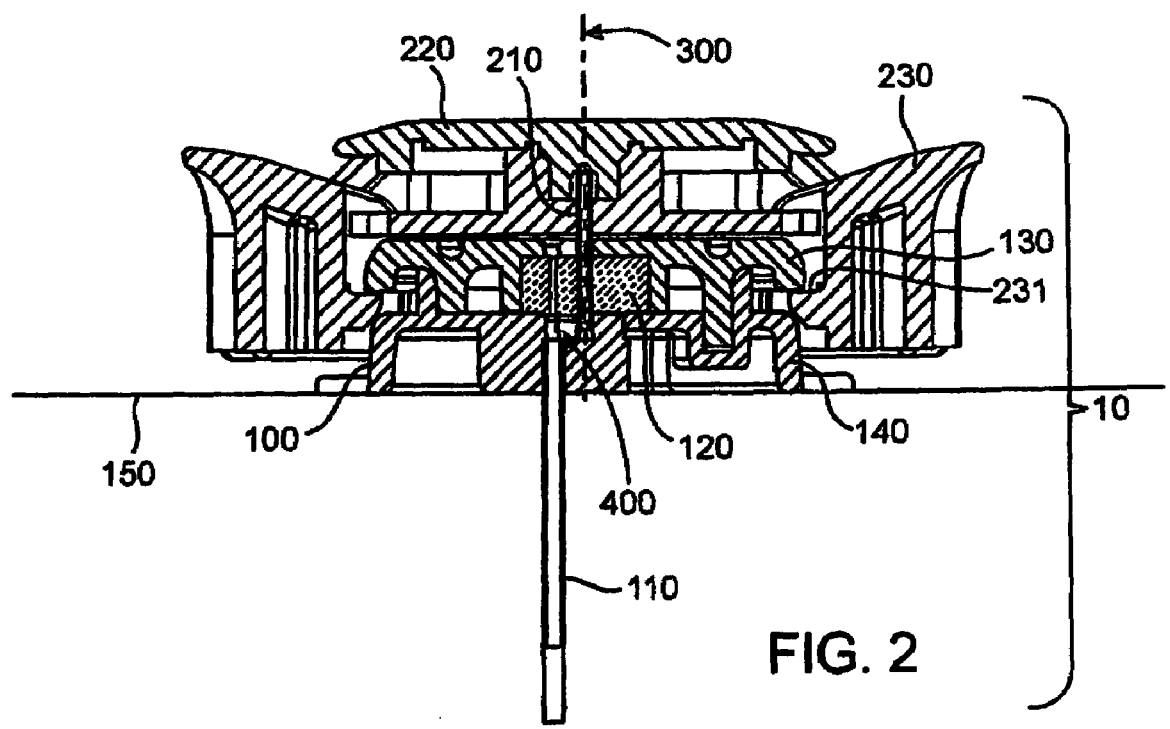
FIG. 2 is a sectional side elevation view of the present invention with the connecting hub attached to the housing.

When connecting hub 200 is attached on top of housing 100 (as shown in FIG. 2), infusion needle 210 penetrates septum 120 thereby forming a flow path 400 between infusion needle 210 and infusion cannula 110, in the preferred embodiment being a lateral passageway. As will be explained herein, infusion needle 210 is preferably in fluid communication with an infusion tube connected to the side of connecting hub 200, to supply medication infusion therethrough. Because cannula 110 is on one axis and the infusion needle 210 is along another axis and not collinear, it is possible for the entire body to be shallower than if the two axes were aligned. The preferred arrangement has the needle 210 and cannula parallel but in different planes. They need not be parallel. The infusion needle could be inserted at an angle off vertical (such as an oblique angle), so long as it reaches the passageway (flow path) 400 so that fluid communication therebetween can occur.

A further advantage of the design shown in FIG. 2 is that connecting hub 200 may be freely rotatable with respect to housing 100 even after connecting hub 200 has been attached to housing 100. This is because infusion needle 210 is preferably positioned in the center of device 10 (i.e.: co-linear with axis 300) and because tabs 231 may be freely moveable along through notch 135 (which runs around housing 100 between upper and lower portions 130 and 140 respectively). As a result, connecting hub 200 may freely rotate to different radial positions with respect to housing 100 since connecting hub 200 simply rotates around centrally-located infusion needle 210 while tabs 231 slide around within notch 135 around the perimeter of housing 100. In optional embodiments, stops (not shown) may be positioned around notch 135 to limit rotation of connecting hub 200 with respect to housing 100. As a result, the present invention is understood to encompass embodiments wherein connecting hub 200 is fully rotatable 360 degrees with respect to housing 100, or rotatable less than 360 degrees with respect to housing 100, or wherein connecting hub 200 is not rotatable with respect to housing 100 at all. Consequently, the present invention encompasses embodiments wherein connecting hub 200 is attachable to housing 100 at different rotational positions.

Figure 3:
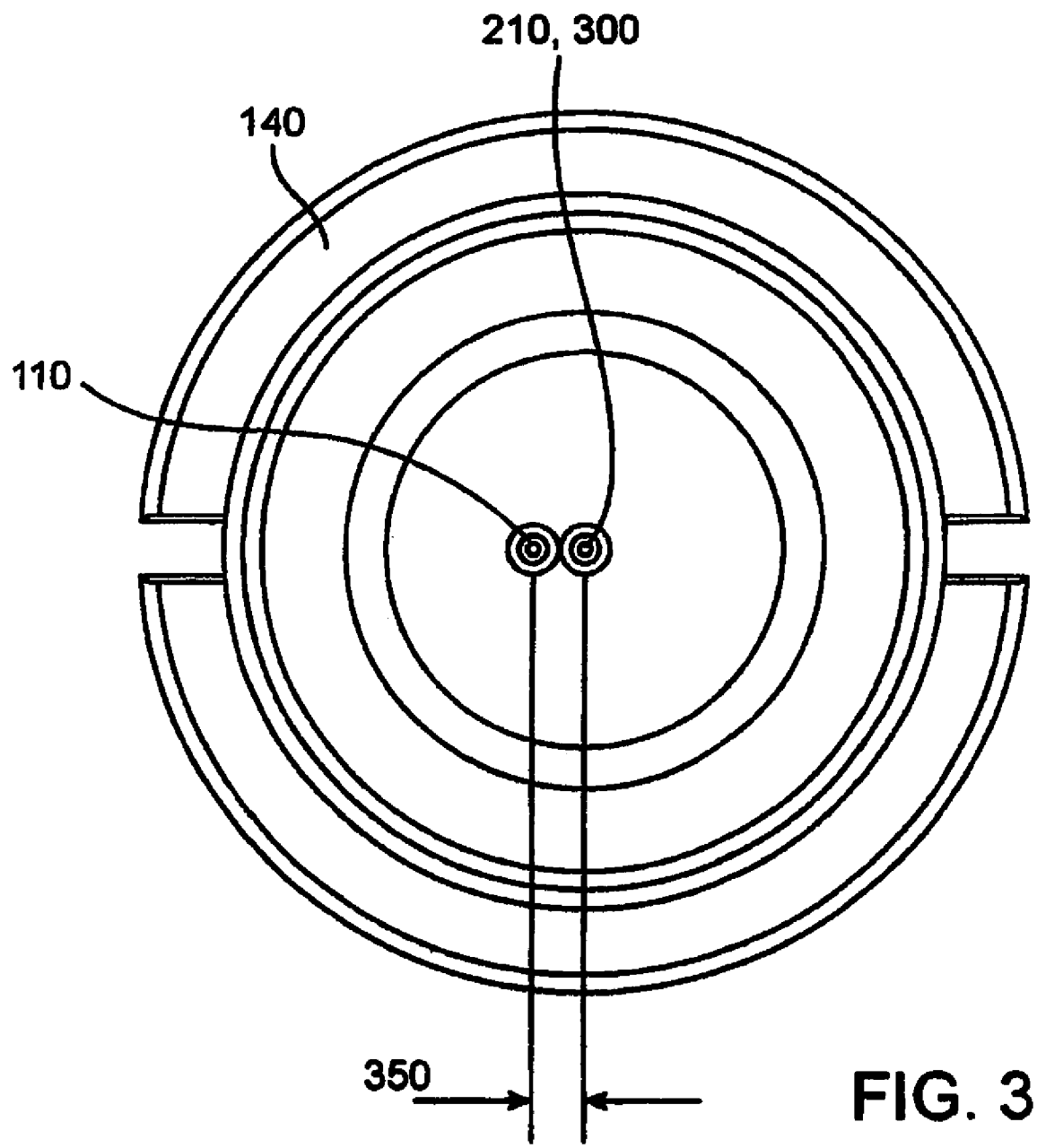
FIG. 3 is a bottom plan view of the lower portion of the housing of the present invention.

FIG. 3 shows a bottom plan view of lower portion 140 of housing 100. The offset distance 350 between infusion cannula 110 and infusion needle 210 is clearly seen. In such preferred embodiments, infusion cannula 110 and infusion needle 210 are positioned parallel to one another. In most preferred embodiments, infusion needle 210 is disposed in the center of connecting hub 200 (i.e.: along axis 300) and the infusion cannula 110 is disposed off-center to the housing (i.e. not along axis 300); however, the present invention is not so limited.

Figure 4:
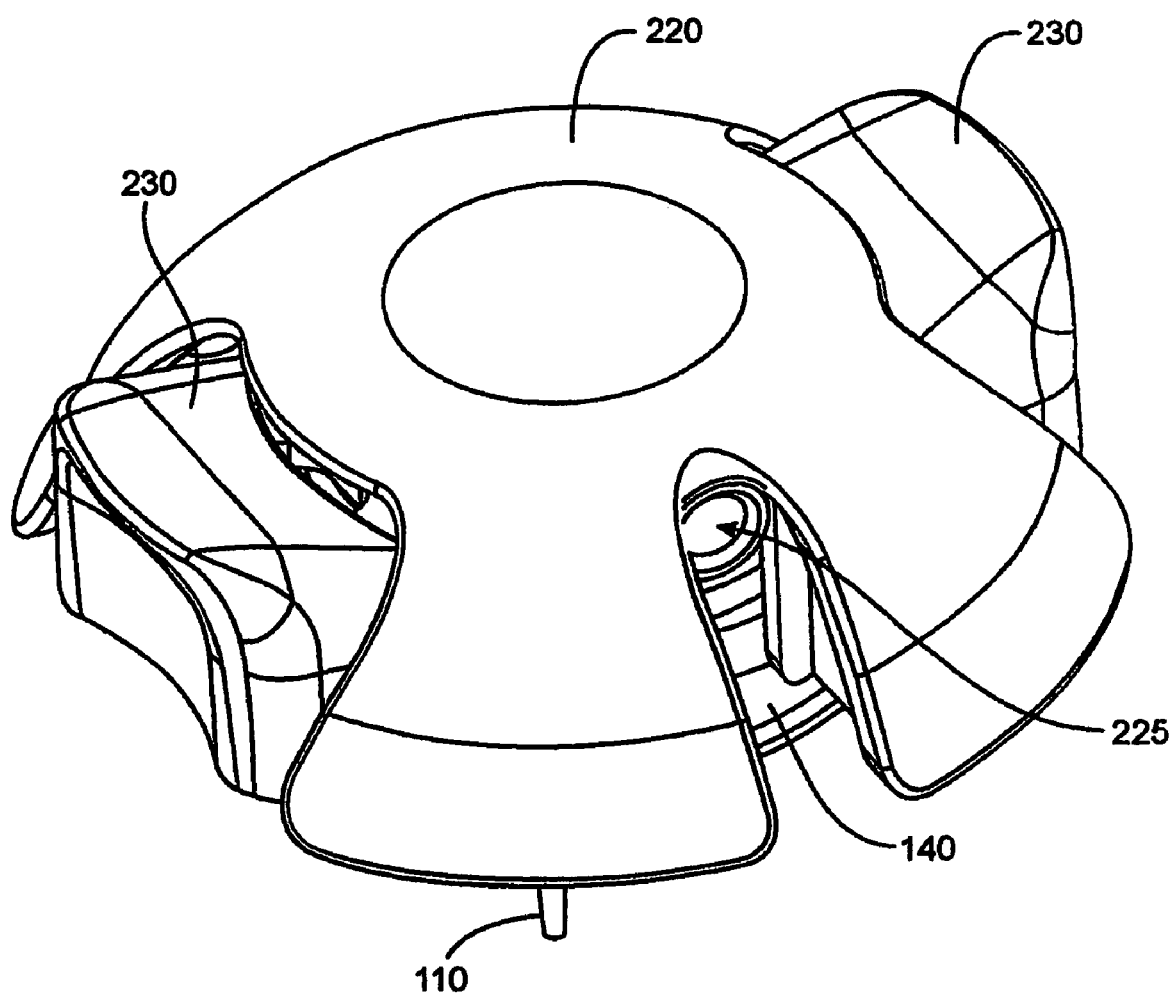
FIG. 4 is a top perspective view of the present invention, showing the connecting hub with flexible handles attached thereto.

FIG. 4 shows a top perspective view of main body 220 of connecting hub 200. Flexible handles 230 are also seen. Connecting hub 200 further includes a side infusion port 225. An infusion tube 215 (FIG. 9) connected into infusion port 225 is in fluid communication with infusion needle 210. Thus, fluid entering connecting hub 200 through infusion port 225 passes directly through infusion needle 210, and then through septum 120, across flow path 400, and then down through infusion cannula 110, and into the patient.

In preferred embodiments, infusion cannula 110 and infusion needle 210 may have different diameters. It is to be understood, therefore, that the present invention encompasses embodiments where infusion cannula 110 is either larger or smaller in diameter than infusion needle 210, and also encompasses embodiments where infusion cannula 110 has the same diameter than infusion needle 210.

Figure 5:
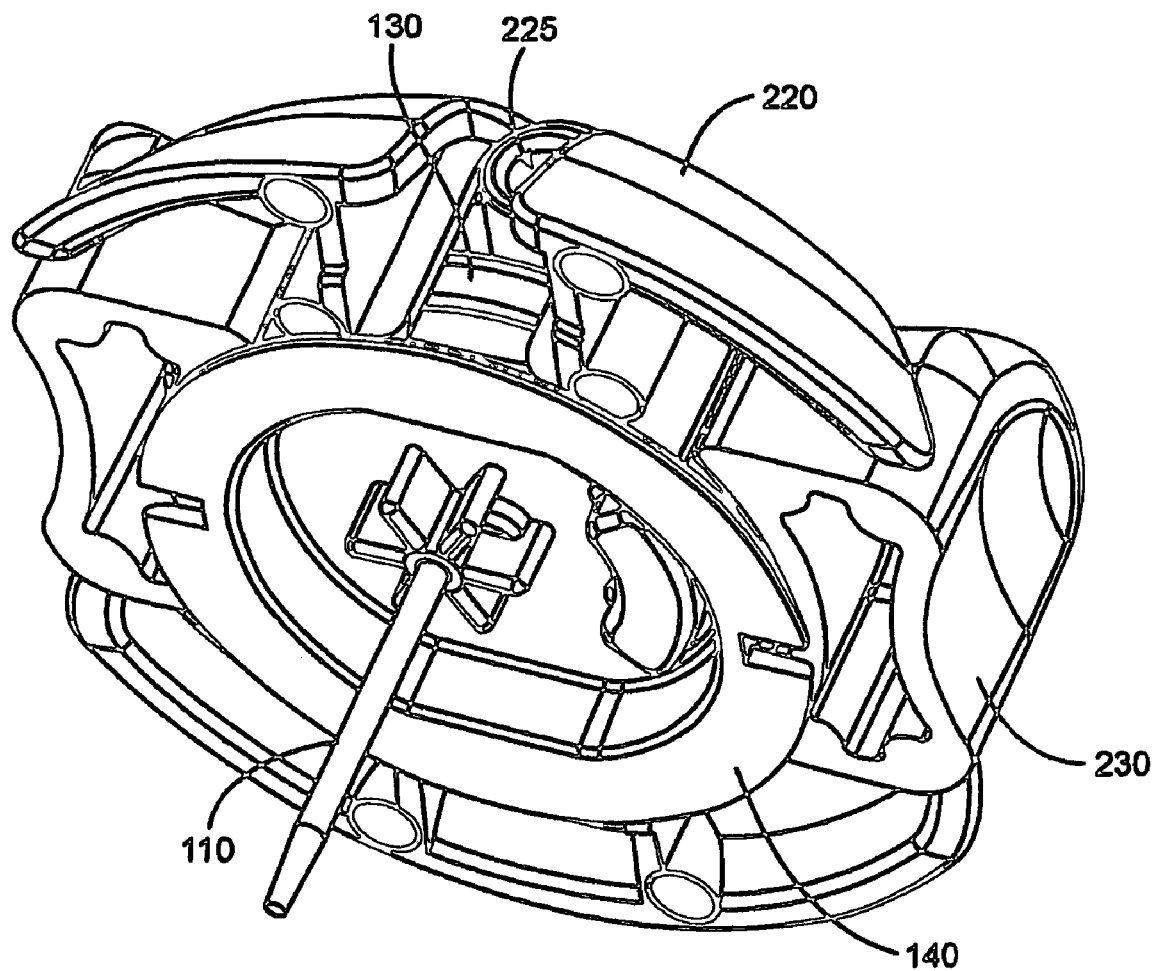
FIG. 5 is a bottom perspective view of the present invention with the adhesive bandage removed.

FIG. 5 shows further details of the bottom of assembled infusion device 10.

Figure 6:
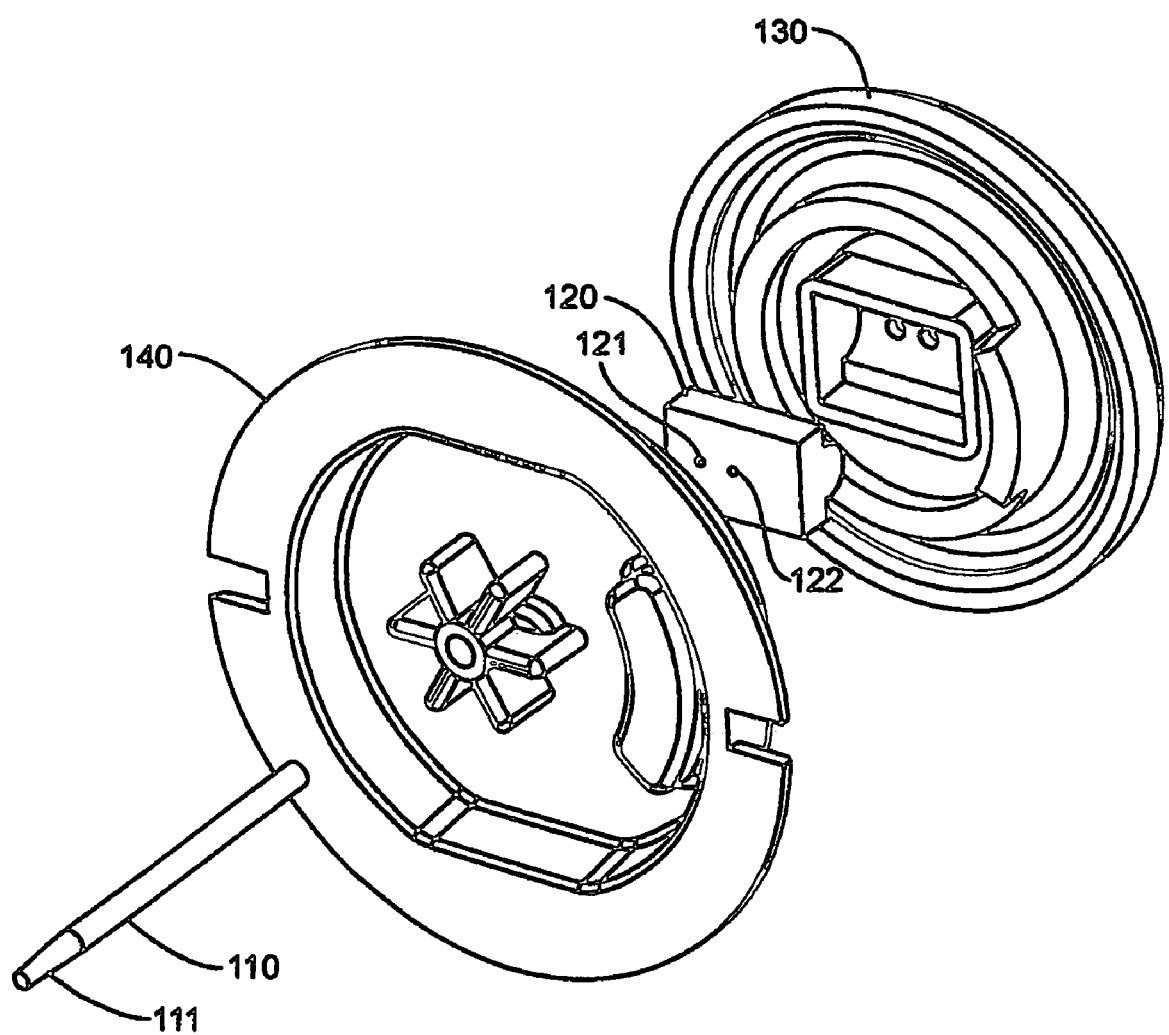
FIG. 6 is a bottom exploded perspective view of the housing of the present invention.
Figure 7:
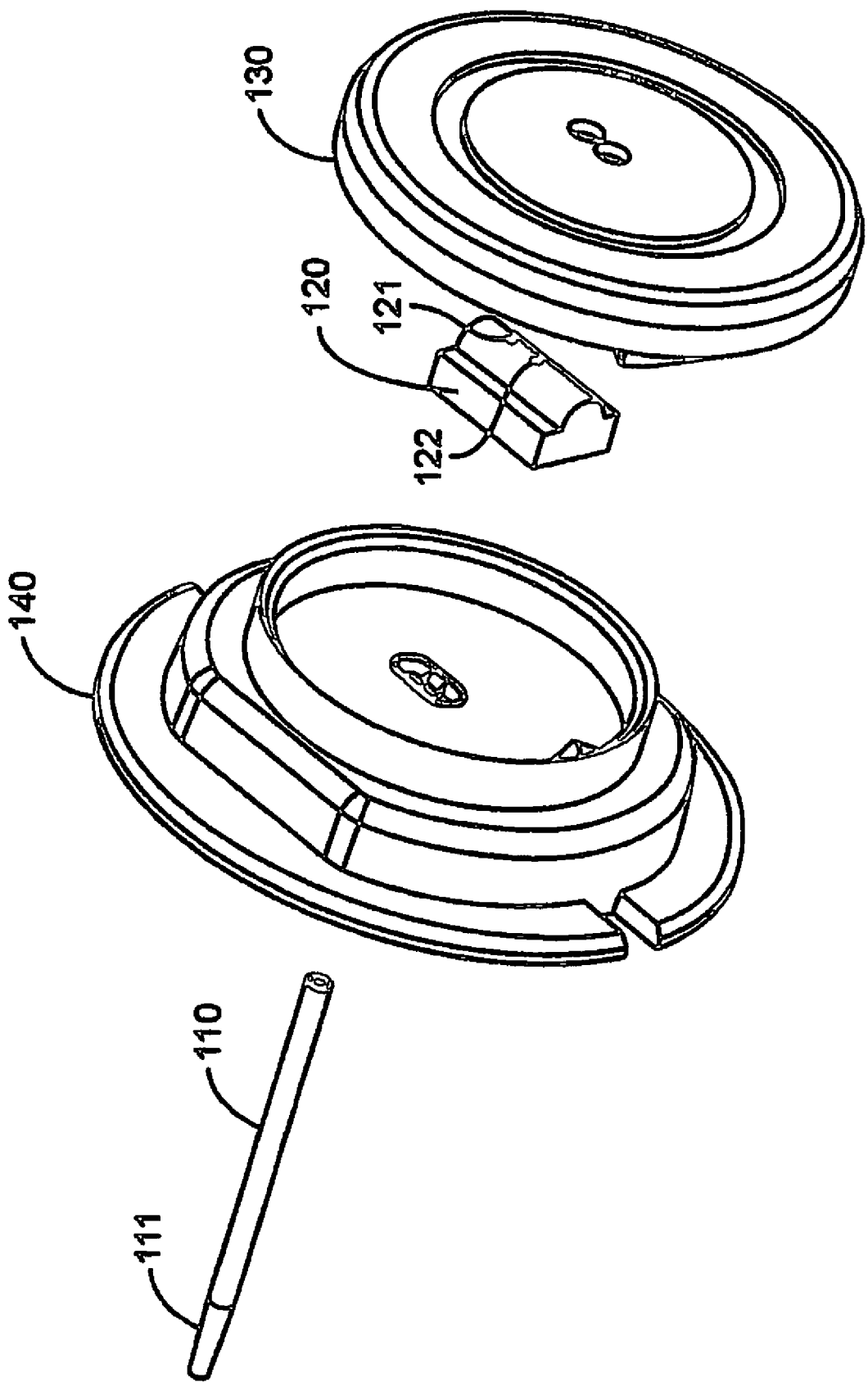
FIG. 7 is a top exploded perspective view of the housing of the present invention.

FIGS. 6 and 7 shows the narrowed distal end 111 of infusion cannula 110, which minimizes discomfort to the patient when infusion cannula 110 pierces the patient's skin. FIG. 6 also shows further details of septum 120. Specifically, an insertion needle 510 (FIGS. 10 to 12) passes through septum 120 at location 121; whereas infusion needle 210 passes through septum 120 at location 122.

Figure 8:
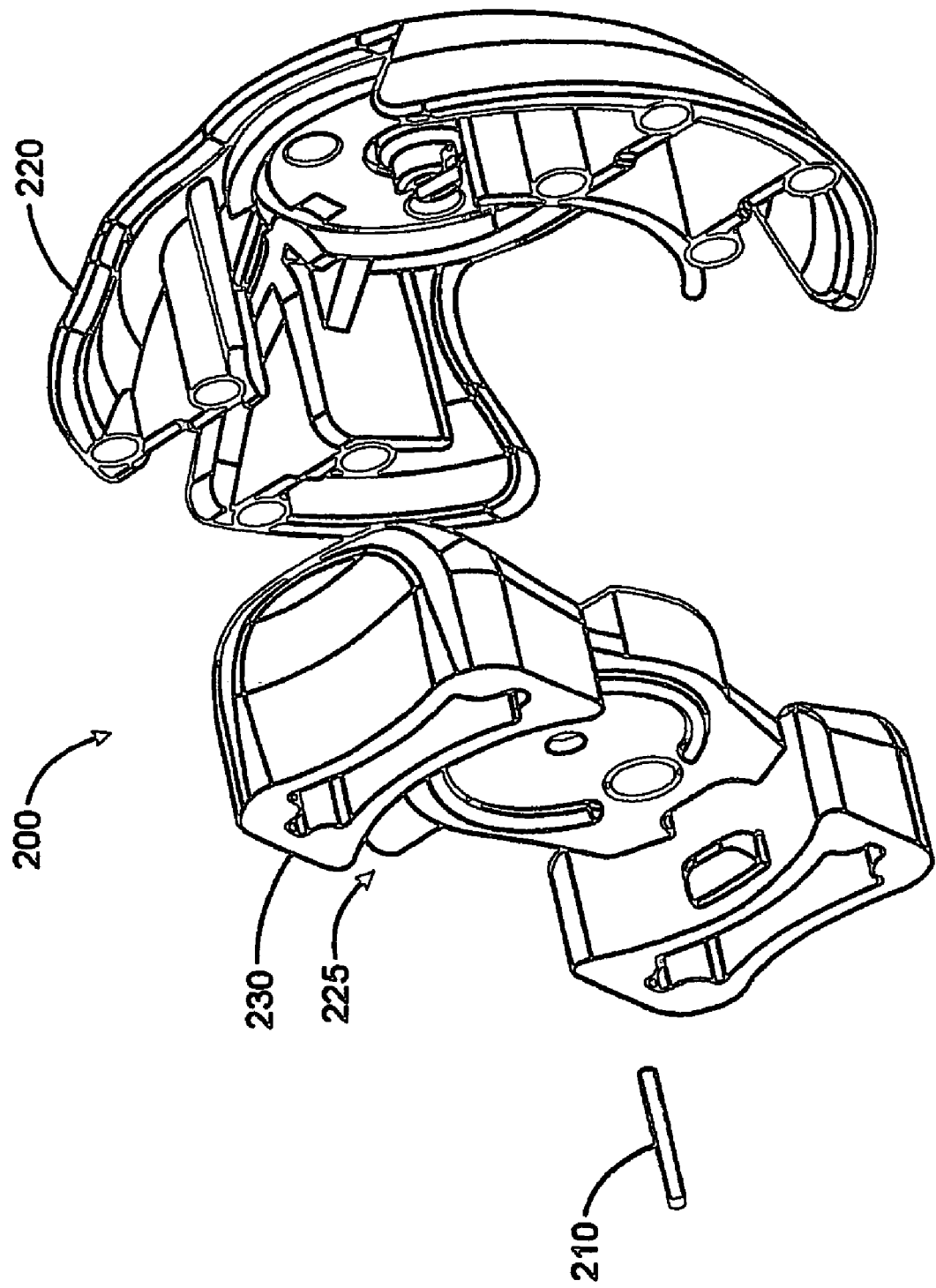
FIG. 8 is a bottom exploded perspective view of the connecting hub of the present invention.
Figure 9:
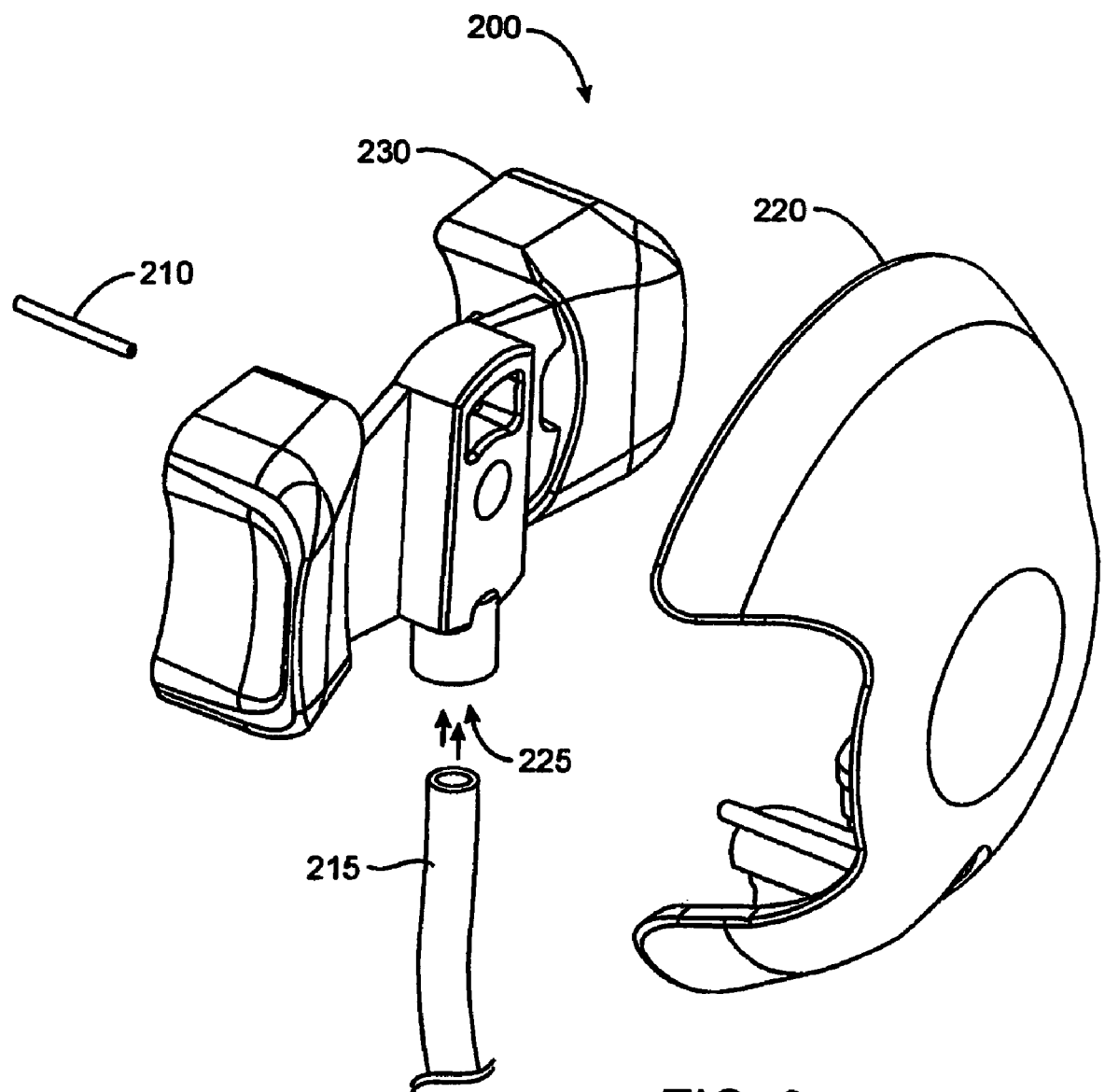
FIG. 9 is a top exploded perspective view of the connecting hub of the present invention.

FIGS. 8 and 9 show further details of connector hub 200 and flexible handles 230. As shown in FIG. 9, a fluid infusion tube 215 may be connected into infusion port 225.

Thus, fluid introduced into infusion port 225 by fluid infusion tube 215 will pass out of infusion needle 210.

Figure 10:
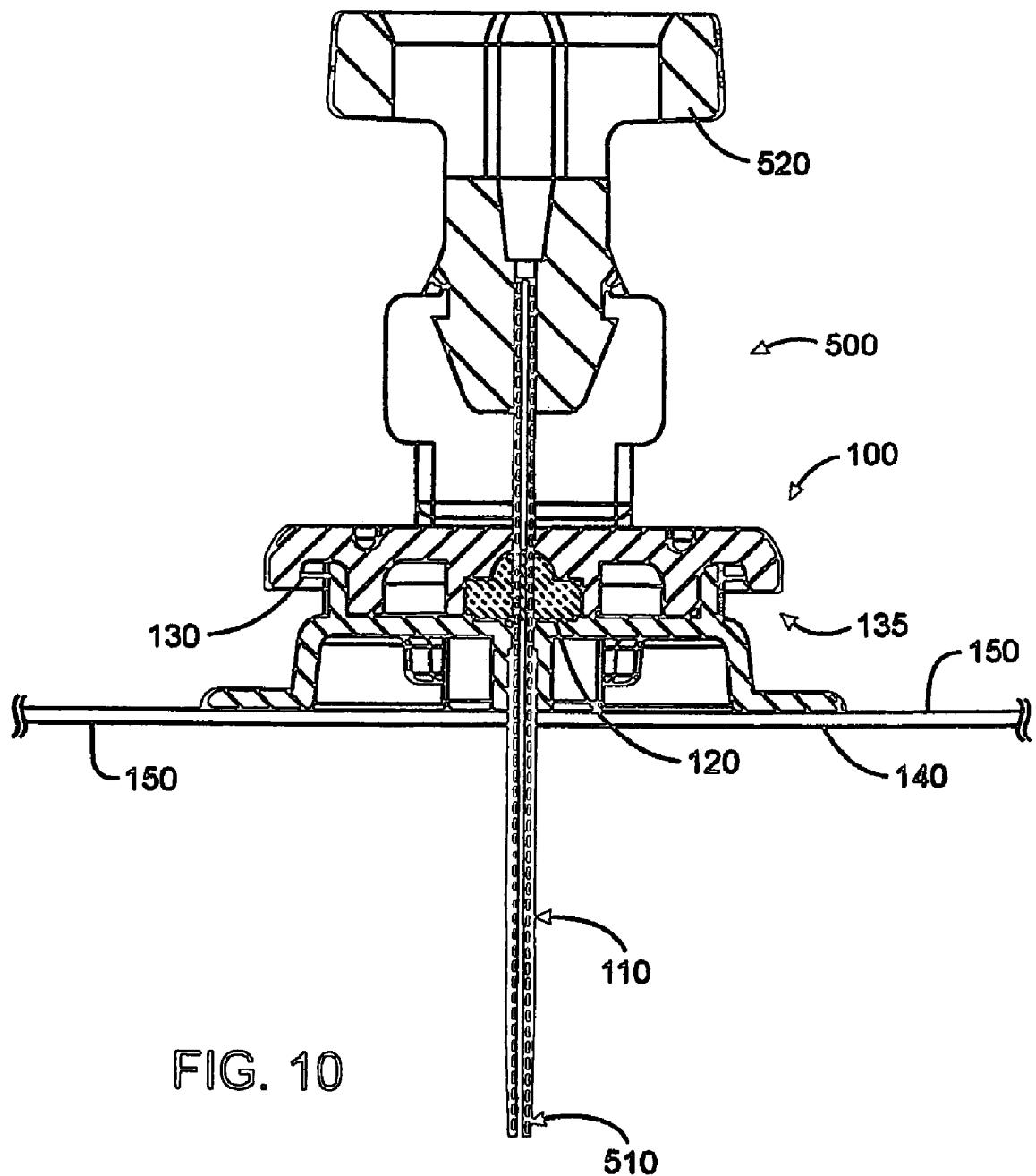
FIG. 10 is a sectional side elevation view of the housing with a positioning needle assembly sitting thereon, with a positioning needle received through the infusion cannula

FIG. 10 shows an insertion needle assembly 500 which is used for positioning housing 100 against the patient's skin. Insertion needle assembly 500 includes an insertion needle 510 which is initially positioned to extend through infusion cannula 110, passing through septum 120 at location 121, as shown.

Insertion needle assembly 500 further includes a handle assembly 520. The patient typically uses a spring loaded inserter (not shown) that advances handle assembly 520 thereby pressing housing 100 downward against their skin such that infusion cannula 110 and insertion needle 510 together pierce through the patient's skin Such downward motion continues until adhesive bandage 150 is pressed firmly against the patient's skin. Then, the spring loaded inserter (not shown) is removed, and handle 520 is pulled upwardly by the patient away from their skin, thus pulling insertion needle 510 out of infusion cannula 110. The remaining hollow infusion cannula 110 is then used to infuse medication into the patient. Once the needle 510 is removed, that passageway therethrough is no longer required. Instead infusate will pass through the offset infusion needle 210 across the lateral flow path 400 and into cannula 110.

Figure 11:
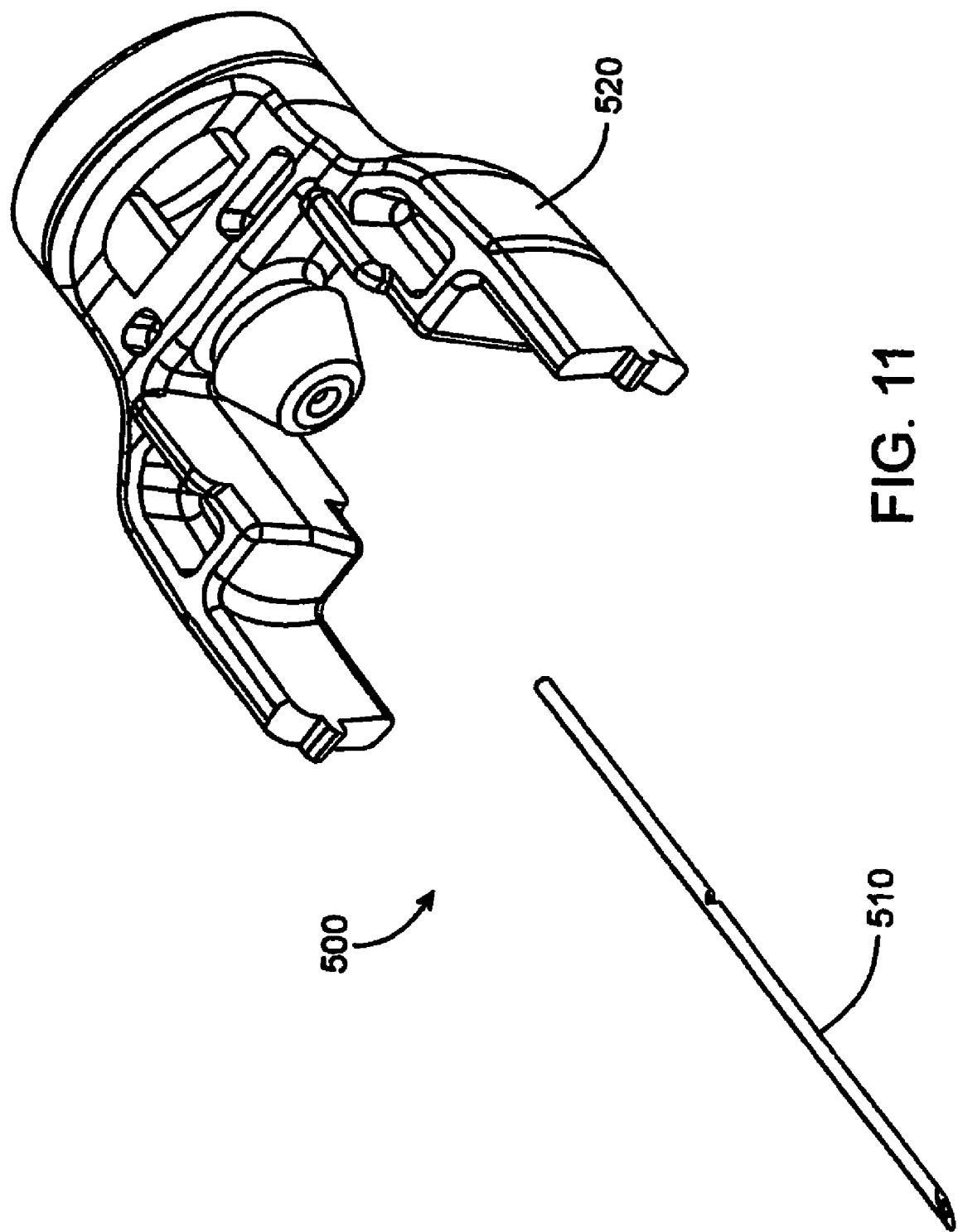
FIG. 11 is a bottom exploded perspective view of the positioning needle assembly.
Figure 12:
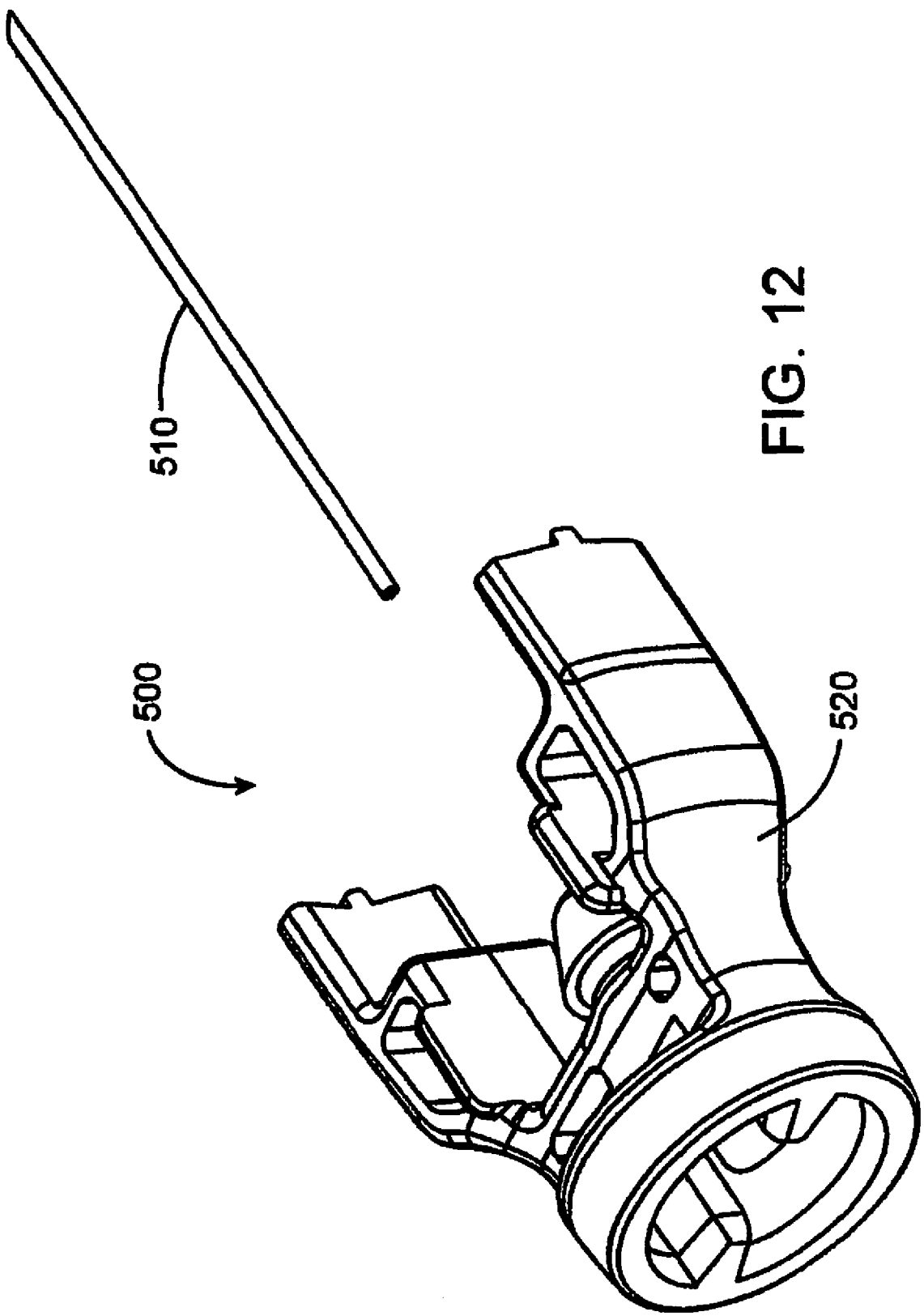
FIG. 12 is a top exploded perspective view of the positioning needle assembly.

FIGS. 11 and 12 show further details of insertion needle assembly 500.

In an alternate embodiment of the present invention, the septum is instead positioned in the connecting hub and the infusion needle is instead disposed in the housing. In such embodiment, the flow path between the infusion needle and the infusion cannula is within the connecting hub, not within the housing.

In an alternate embodiment, septum 120 is pre-slit and infusion needle 210 comprises a hollow tube, which may optionally be made of plastic.

The present invention also encompasses a method of infusing fluid into a patient, by: positioning an infusion housing 100, having a passageway 400, against a patient's skin, such that an infusion cannula 110 extends downwardly away from the infusion housing 100 penetrates the patient's skin along a first axis, thereby providing a pathway for infusate into the patient; and inserting an infusion needle 210 into housing 100 along an axis 300 adjacent, but not identitical with said first axis; and causing infusate to pass through insertion needle 210, into passageway 400 and then into infusion cannula 110.

What is claimed is:

1. An infusion device, comprising: a housing configured to be applied to tissue; an infusion cannula extending downwardly away from the housing and capable of receiving an insertion needle; a septum disposed in the housing; a passageway under said septum and in fluid communication with said cannula and; an infusion needle insertable through the septum, the infusion needle capable of penetrating the septum and entering said passageway thereby forming a flow path between the infusion needle and the infusion cannula and wherein the infusion cannula and the infusion needle are aligned on separate non identical axes with the insertion needle being substantially perpendicular to the tissue so that it needle is axially rotatable with respect to thereto.

2. The device of claim 1, wherein the infusion cannula and the infusion needle are positioned parallel to one another.

3. The device of claim 1, wherein the infusion cannula and the infusion needle are positioned offset from one another.

4. The device of claim 1, wherein the infusion cannula and the infusion needle are in different planes relative to each other.

5. The device of claim 1, wherein the infusion cannula and the infusion needle are at oblique angles relative to each other.

6. The device of claim 1, further including a connecting hub rotatably connected to the housing and wherein the infusion needle is disposed in the center of the connecting hub and the infusion cannula is disposed off-center to the housing.

7. The device of claim 1, wherein the infusion cannula and the infusion needle have different diameters.

8. The device of claim 1, further including a connecting hub which is rotatable with respect to the housing.

9. The device of claim 8, wherein the connecting hub is rotatable 360 degrees with respect to the housing.

10. The device of claim 8, wherein the connecting hub is rotatable less than 360 degrees with respect to the housing.

11. The device of claim 1, further including a connecting hub which is attachable to the housing at different rotational positions.

12. The device of claim 1, further including a connecting hub which further comprises: at least one flexible handle configured to attach the connecting hub onto the housing.

13. The device of claim 1, wherein the housing further comprises: an adhesive bandage extending therefrom for holding the housing against the patient's skin.

14. The device of claim 1, wherein the connecting hub further comprises: a fluid infusion tube extending from the connecting hub, the fluid infusion tube being in fluid communication with the infusion needle.

15. The device of claim 1, wherein the septum is pre-slit and wherein the infusion needle is a plastic tube.

16. A method of infusing fluid into a patient, comprising: positioning an infusion housing, having a passageway, against a patient's skin, such that an infusion cannula extends downwardly away from the infusion housing penetrates the patient's skin along a first axis, thereby providing a pathway for infusate into the patient; and inserting an infusion needle into the housing along a second axis adjacent, making said infusion need rotatable along said second access, said second axis being not identical with said first axis; and causing infusate to pass through said insertion needle, into said passageway and then into said infusion cannula.

17. The method of claim 16, wherein the passageway in the infusion housing is a lateral passageway.

18. An infusion device, comprising:

a housing; a connecting hub rotatable on said housing; stops configured to limit the rotation of the hub; an infusion cannula extending downwardly away from the housing and capable of receiving an insertion needle; a septum disposed in the housing; a passageway under said septum and in fluid communication with said cannula and; an infusion needle insertable through the rotatable hub and the septum, the infusion needle capable of penetrating the septum and entering said passageway thereby forming a flow path between the infusion needle and the infusion cannula and wherein the infusion cannula and the infusion needle are aligned on separate non identical generally axes and where the connecting hub is rotatable between said stops.

* * * * *